United States Patent [19]
Cordi et al.

[11] Patent Number: 5,646,132
[45] Date of Patent: Jul. 8, 1997

[54] NEW 2(1H)-QUINOLONE COMPOUNDS

[75] Inventors: Alex Cordi, Suresnes; Patrice Desos, Courbevoie; Jean Lepagnol, Chaudon, all of France

[73] Assignee: Adir et Compagnie, Courbevoie, France

[21] Appl. No.: 499,946

[22] Filed: Jul. 10, 1995

Related U.S. Application Data

[62] Division of Ser. No. 297,793, Aug. 30, 1994, Pat. No. 5,536,709.

[30] Foreign Application Priority Data

Aug. 31, 1993 [FR] France ................. 93 10379

[51] Int. Cl.$^6$ ................. A61K 31/675
[52] U.S. Cl. ................. 514/82; 514/89; 514/312
[58] Field of Search ................. 514/312, 82, 89

[56] References Cited

U.S. PATENT DOCUMENTS

| | | | |
|---|---|---|---|
| 4,124,558 | 11/1978 | Hardtmann et al. | 546/21 |
| 4,898,854 | 2/1990 | Hutchison et al. | 514/89 |

*Primary Examiner*—Ba K. Trinh
*Attorney, Agent, or Firm*—The Firm of Gordon W. Hueschen

[57] ABSTRACT

Compound of formula (I):

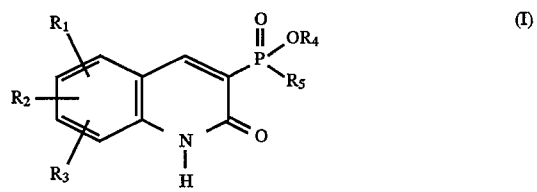

in which:

$R_1$, $R_2$ and $R_3$, which are identical or different, represent hydrogen or halogen or alkyl, nitro, cyano or aminosulfonyl, or alternatively, when two of them are located on adjacent carbons, form, with the carbon atoms to which they are attached, ($C_3$–$C_7$) cycloalkyl ring or substituted or unsubstituted benzene ring, $R_4$ represents hydrogen, linear or branched ($C_1$–$C_6$) alkyl, substituted or unsubstituted phenyl or a group

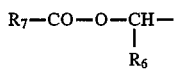

in which $R_6$ and $R_7$, which are identical or different, represent hydrogen or substituted or unsubstituted, linear or branched ($C_1$–$C_6$) alkyl, $R_5$ represents hydrogen, hydroxyl, linear or branched ($C_1$–$C_6$) alkoxy, phenoxy, mercapto, linear or branched ($C_1$–$C_6$) alkylthio, substituted or unsubstituted, linear or branched ($C_1$–$C_6$) alkyl, substituted or unsubstituted phenyl or substituted or unsubstituted amino, or a group

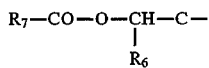

in which $R_6$ and $R_7$ are as defined above, their isomers as well as their addition salts with a pharmaceutically acceptable acid or base, and medicinal product containing the same are useful as inhibitor of the pathological phenomena associated with hyperactivation of the excitating amino acid-dependant pathways of neurotransmission.

9 Claims, No Drawings

NEW 2(1H)-QUINOLONE COMPOUNDS

The present application is a division of our prior-filed application Ser. No. 08/297,793, filed Aug. 30, 1994, now U.S. Pat. No. 5,536,709.

The present invention relates to new 2(1H)-quinolone compounds.

A few 2(1H)-quinolone derivatives have been described in the literature. This applies, for example, to the compounds described by C. ALABASTER et al. (J. Med. Chem., 31, 2048–2056, 1988) which are cardiac stimulators, or to those described by F. BAHR et al. (Pharmazie, 36, H.10, 1981).

The compounds described in the present invention, apart from the fact that they are new, display especially advantageous pharmacological properties: they are potent inhibitors of the phenomena linked to the hyperactivation of excitatory amino acids.

L-Glutamic acid and L-aspartic acid have the capacity to activate the neurons of the central nervous system, and many studies have demonstrated that these excitatory amino acids (EAA) satisfy the criteria that define a neurotransmitter. For this reason, the modulation of neuronal events associated with these EAA appears to be an advantageous target for the treatment of neurological diseases.

In effect, it has been demonstrated that excessive release of EAA and hyperstimulation of their receptors is probably one of the causes of the neuronal degeneration observed in epilepsy, senile dementia or strokes. At the present time, there is an ever-increasing number of neurodegenerative diseases in which EAA are closely implicated (Huntington's chorea, schizophrenia, amyotrophic lateral sclerosis) (McGEER E. G. et al., Nature 263, 517–519, 1976; SIMON R. et al., Science 226, 850–852, 1984).

Furthermore, while it is certain that hyperactivation of EAA-dependent neurotransmission exerts neurotoxic effects, the normal activation of this neurotransmission facilitates mnemic and cognitive performance (LYNCH G. & BAUDRY M., Science, 224, 1057–1063, 1984; ROTHMAN S. M. & OLNEY J. W., Trends in Neuro Sci., 10, 299–302, 1987). From a pharmacological and therapeutic standpoint, it is hence appropriate to counteract only pathological stimulations while not impairing the physiological level of activation.

The EAA receptors localized post- and presynaptically have been classified in 4 groups in accordance with the affinity and the electrophysiological an/or neurochemical effects of specific ligands:

NMDA (N-methyl-D-aspartate) receptor associated with an ion channel permeable to mono- and divalent cations (including calcium) but which is blocked by magnesium. Accumulation of calcium in the cell is considered to be one of the causes of neuronal death. Opening of the NMDA channel is regulated by several sites associated with the receptor and, in particular, is promoted by glycine, the effect of which is strychnine-insensitive. This glycine site constitutes one of the important targets for modulating the activation of the NMDA receptor.

AMPA (α-amino-3-(hydroxy-5-methyl-4-isoxazolepropionic acid) receptor associated with an ion channel permeable to monovalent cations including sodium. Activation of this channel is considered to bring about a membrane depolarization.

kainate receptor, the ionic characteristics of which are akin to those of the AMPA receptor but which differs therefrom by the level of conductance and desensitization. However, a large number of studies are tending to demonstrate that the AMPA receptor and the kainate receptor have close structural and functional analogies and constitute a single receptor family (KEINANEN K. et al., Science, 249, 556–560, 1990).

ACPD (trans-1-aminocyclopentanedicarboxylic acid) receptor, referred to as a metabotropic receptor since it is not coupled to an ion channel.

Activation of the ionotropic receptors by EAA opens the ion channels and, in particular, permits the entry of sodium, which depolarizes the cell. This first phase, which involves the AMPA receptor, then leads to hyperactivation of the NMDA receptor and to the massive accumulation of calcium (BLAKE J. F. et al., Neurosci. Letters, 89, 182–186, 1988; BASHIR Z. I. et al., Nature 349, 156–158, 1991).

The compounds of the present invention or the products of their metabolic hydrolysis (prodrugs) are hence directed, in a novel manner, towards counteracting the excitatory and toxic effects of EAA by blocking the initial activation of the AMPA/kainate receptor.

The compounds of the present invention are hence useful as inhibitors of the pathological, in particular neurotoxic, phenomena associated with hyperactivation of the excitatory amino acid-dependent pathways of neurotransmission. They stand out with respect to products described by European Patent Application EP 542,609 in that they are particularly soluble in water, are entirely colorless and that they have a good cerebral bioavailability after systemic administration.

They are hence potential therapeutic agents for the treatment of neurological and mental diseases involving these amino acids: acute or chronic degenerative diseases, such as stroke, cerebral or spinal trauma or epilepsy or chronic neurodegenerative diseases such as Alzheimer's disease, schizophrenia, amyotrophic lateral sclerosis or Huntington's chorea.

More specifically, the present invention relates to the compounds of formula (I):

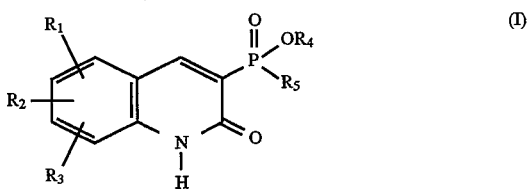

in which:

$R_1$, $R_2$ and $R_3$, which are identical or different, represent a hydrogen or halogen atom, a linear or branched ($C_1$–$C_6$) alkyl group (unsubstituted or substituted with one or a number of halogen atoms) or a nitro, cyano or a aminosulfonyl group, or alternatively, when two of them are located on adjacent carbons, form with the carbon atoms to which they are attached, a ($C_3$–$C_7$) cycloalkylkene ring or a benzene ring (unsubstituted or substituted with one or a number of halogen atoms or linear or branched ($C_1$–$C_6$) alkyl, linear or branched ($C_1$–$C_6$) alkoxy or trihalomethyl groups), $R_4$ represents a hydrogen atom, a linear or branched ($C_1$–$C_6$) alkyl group, a phenyl group (unsubstituted or substituted with one or a number of halogen atoms or linear or branched ($C_1$–$C_6$) alkyl, linear or branched ($C_1$–$C_6$) alkoxy or trihalomethyl groups) or a group

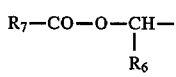

in which $R_6$ and $R_7$, which are identical or different, represent a hydrogen atom or a linear or branched ($C_1$–$C_6$) alkyl group (unsubstituted or substituted with a ($C_3$–$C_7$) cycloalkyl or phenyl group), $R_5$ represents a hydrogen atom, a hydroxyl, linear or branched ($C_1$–$C_6$) alkoxy, phenoxy, mercapto, linear or branched ($C_1$–$C_6$) alkylthio, linear or branched ($C_1$–$C_6$) alkyl (unsubstituted or substituted with a ($C_3$–$C_7$) cycloalkyl group), phenyl (unsubstituted or substituted with one or a number of halogen atoms or linear or branched ($C_1$–$C_6$) alkyl, linear or branched ($C_1$–$C_6$) alkoxy or trihalomethyl groups) or amino (unsubstituted or substituted with one or two linear or branched ($C_1$–$C_6$) alkyl groups) group or a group

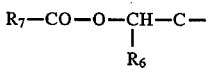

in which $R_6$ and $R_7$ are as defined above, to their isomers as well as to their addition salts with a pharmaceutically acceptable acid or base.

Mention may be made, among pharmaceutically acceptable bases and without implied limitation, of sodium hydroxide, potassium hydroxide, tert-butylamine, diethylamine, ethylenediamine and the like.

The invention also encompasses the process for preparing the compounds of formula (I), wherein a compound of formula (II):

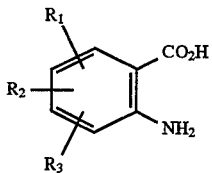

in which $R_1$, $R_2$ and $R_3$ have the same meaning as in the formula (I), is used as starting material, which starting material is reduced, depending on the nature of the substituents $R_2$, $R_3$ and $R_4$, either in an aprotic medium in the presence of lithium aluminum hydride, aluminum hydride, diborane or borane complexes, or in an acidic protic medium when sodium cyanoborohydride is used, to yield an alcohol of formula (III):

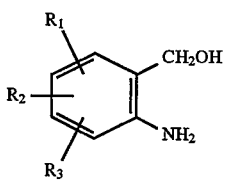

in which $R_1$, $R_2$ and $R_3$ have the same meaning as in the formula (I), which is oxidized using a metal oxide in an inert solvent, an alkali metal hydrohalate in a protic solvent or an acid chloride in dimethyl sulfoxide, to yield the aldehyde of formula (IV):

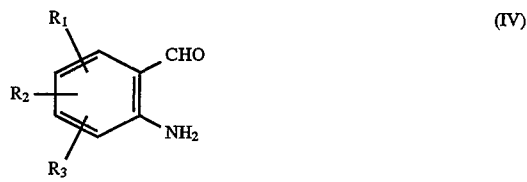

in which $R_1$, $R_2$ and $R_3$ have the same meaning as in the formula (I), which is then condensed with an alkyl malonate of formula (V), in a protic medium, in the presence of an alkali metal alkoxide, a tertiary amine or an alkali metal hydroxide:

in which alk represents a linear or branched ($C_1$–$C_6$) alkyl group, to yield an ester of formula (VI):

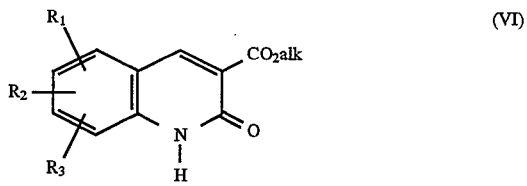

in which $R_1$, $R_2$, $R_3$ and alk have the same meaning as above, which is converted to the corresponding acid of formula (VII):

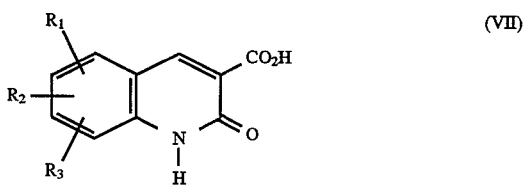

in which $R_1$, $R_2$ and $R_3$ have the same meaning as in the formula (I), which is reacted in the presence of bromine in pyridine to yield the compound of formula (VIII):

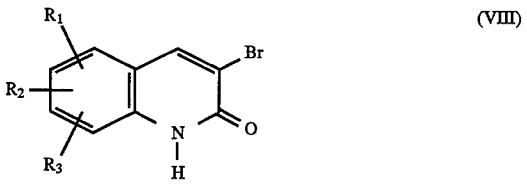

in which $R_1$, $R_2$ and $R_3$ have the same meaning as in the formula (I), the lactam functional group of which is protected by reacting with phosphorus oxychloride followed by reacting with an alkali metal alkoxide in an alcoholic medium, to yield the compound of formula (IX):

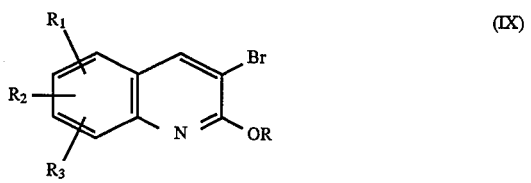

in which $R_1$, $R_2$ and $R_3$ have the same meaning as in the formula (I) and R represents a linear or branched ($C_1$–$C_6$) alkyl group, which is reacted with a dialkyl or a diaryl phosphite in the presence of triethylamine and tetrakis (triphenylphosphine)palladium as catalyst, in an anhydrous medium, according to the technique described by T. HIRAO (Synthesis, 56–57, 1981), to yield the compound of formula (X):

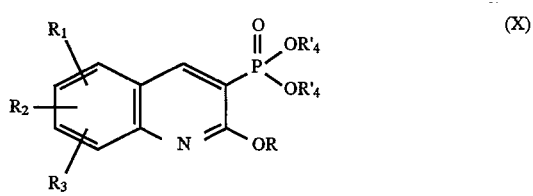

in which $R_1$, $R_2$, $R_3$ and R have the same meaning as above and $R'_4$ represents a linear or branched ($C_1$–$C_6$) alkyl group or an aryl group, which is then:

either entirely deprotected in the presence of trimethylsilyl bromide in an acetonitrile medium and then treated in an acidic medium, to yield the compound of formula (I/a), a specific case of the compounds of formula (I):

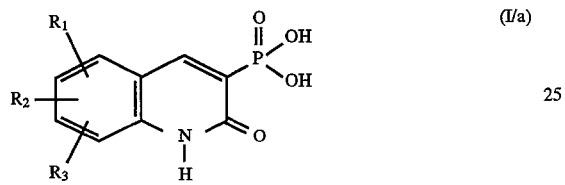

in which $R_1$, $R_2$ and $R_3$ have the same meaning as in the formula (I), which is reacted, if desired, in a basic medium with a halogenated derivative of formula $R''_4$-Cl in which $R''_4$ represents a linear or branched ($C_1$–$C_6$) alkyl group, a phenyl group (unsubstituted or substituted with one or a number of halogen atoms or linear or branched ($C_1$–$C_6$) alkyl, linear or branched ($C_1$–$C_6$) alkoxy or trihalomethyl groups) or a group

in which $R_6$ and $R_7$ have the same meaning as in the formula (I), to yield the compound of formula (I/b), a specific case of the compounds of formula (I),

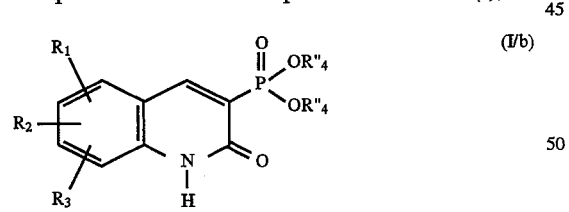

in which $R_1$, $R_2$, $R_3$ and $R''_4$ have the same meaning as above, or partially deprotected by treatment in a basic medium to yield the compound of formula (XI):

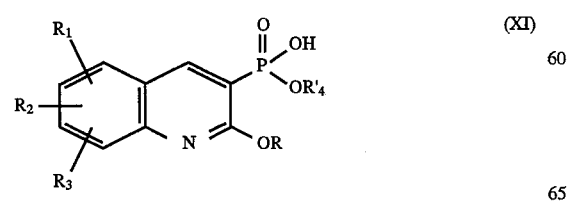

in which $R_1$, $R_2$, $R_3$, R and $R'_4$ have the same meaning as above, which compound of formula (XI):

is subjected, depending on the nature of the compounds of formula (I) which it is desired to obtain, to:

either: a treatment in an acidic medium to yield the compound of formula (I/c), a specific case of the compounds of formula (I):

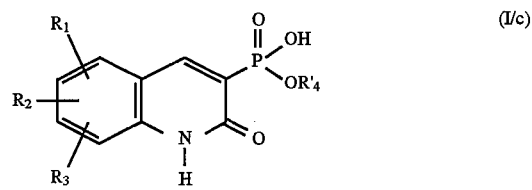

in which $R_1$, $R_2$, $R_3$ and $R'_4$ have the same meaning as above, or alternatively: the action of an alcohol of formula (XII), according to the process described by D. A. CAMPBELL (J. Org. Chem., 57, 6331–6335, 1992):

in which $R'_5$ represents a phenyl or linear or branched ($C_1$–$C_6$) alkyl group, to yield the compound of formula (XIII):

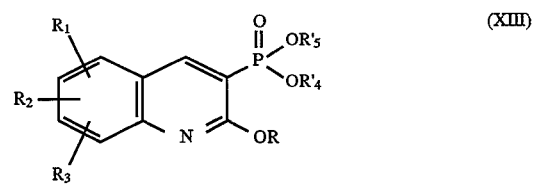

which is selectively deprotected by reacting with trimethylsilyl bromide in an acetonitrile medium and then treatment with hydrochloric acid, to yield the compound of formula (I/d), a specific case of the compounds of formula (I):

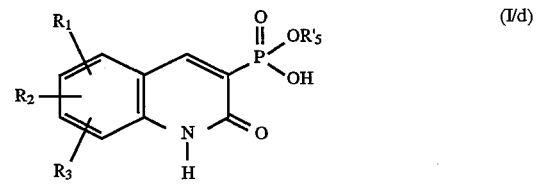

in which $R_1$, $R_2$, $R_3$ and $R'_5$ have the same meaning as above, or yet again: reaction with oxalyl chloride according to the method described by R. S. RODGERS (Tetrahedron Lett., 33, 7473, 1992), to yield the compound of formula (XIV):

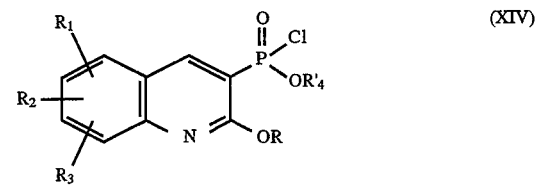

in which $R_1$, $R_2$, $R_3$, R and $R'_4$ have the same meaning as above, which compound of formula (XIV) is then treated:
either with an organomagnesium derivative of formula (XV), in an anhydrous medium:

in which X represents a halogen atom and $R''_5$ represents a linear or branched ($C_1$–$C_6$) alkyl group (unsubstituted or substituted with a ($C_3$–$C_7$) cycloalkyl group) or a phenyl group (unsubstituted or substituted with one or a number of halogen atoms or linear or branched ($C_1$–$C_6$) alkyl, linear or branched ($C_1$–$C_6$) alkoxy or trihalomethyl groups), to yield the compound of formula (XVI):

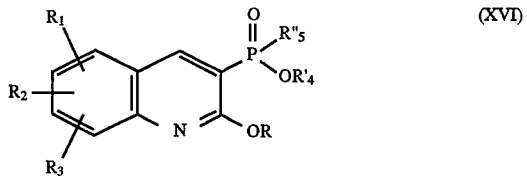

in which $R_1$, $R_2$, $R_3$, R, $R'_4$ and $R''_5$ have the same meaning as above, which is deprotected by reacting with trimethylsilyl bromide in an acetonitrile medium and then treatment with hydrochloric acid, to yield the compound of formula (I/e), a specific case of the compounds of formula (I):

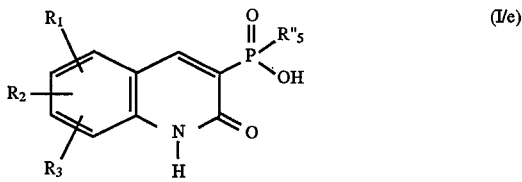

in which $R_1$, $R_2$, $R_3$ and $R''_5$ have the same meaning as above, or which is reacted with a hydride, $H_2S$, alkSH (in which alk means a linear or branched ($C_1$–$C_6$) alkyl group) or ammonia, to yield the compound of formula (XVII):

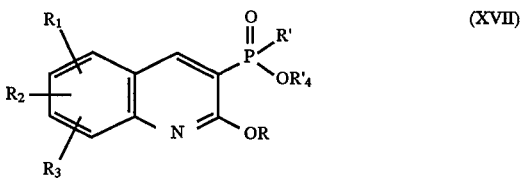

in which $R_1$, $R_2$, $R_3$, R and $R'_4$ have the same meaning as above and R' represents HS—, alkS— or $H_2N$—, or a hydrogen atom, which is deprotected by reacting with trimethylsilyl bromide in an acetonitrile medium and then treatment with hydrochloric acid, to yield the compound of formula (I/f), a specific case of compounds of formula (I):

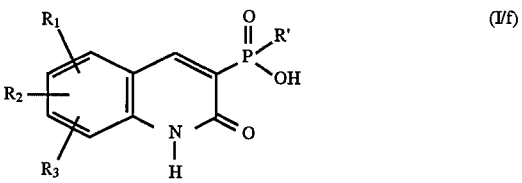

in which $R_1$, $R_2$, $R_3$ and R' have the same meaning as above, which compound of formula (I/a), (I/b), (I/c), (I/d), (I/e) or (I/f)

when $R_1$ and/or $R_2$ and/or $R_3$ represent a hydrogen atom, can undergo electrophilic substitutions according to standard techniques for substitution of aromatic ring-systems, yielding a compound of formula (I) mono-, di- or trisubstituted on the phenyl ring of the quinolone, when $R_1$ and/or $R_2$ and/or $R_3$ represent a nitro group, can undergo a hydrogenation to yield the corresponding amino derivative which, itself, can be, if desired, converted to the corresponding cyano derivative, can be, if appropriate, purified according to a standard purification technique, is separated, if appropriate, into its isomers according to a standard separation technique, is converted, if desired, to its addition salts with a pharmaceutically acceptable acid or base.

The compounds of formula (I) possess very advantageous pharmacological properties. It was possible to study the dual mechanism of action of the compounds of the present invention by means of membrane binding techniques and electrophysiological techniques.

1/ Membrane binding

This is carried out using a rat cortex homogenate. The membrane pellet is prepared in a conventional manner in a sucrose buffer by differential centrifugations, and then frozen until used. After thawing, 200 l of membrane homogenate are taken up in a Tris-HCl (30 mM), $CaCl_2$ (2.5 mM) buffer, pH 7.4, and incubated at 4° C. for 30 minutes in the presence of 25 μl of [$^3$H]-AMPA or [$^3$H]-kainate and 25 μl of the test product. Non-specific binding is determined in the presence of 10 μM quisqualate (AMPA binding) or 10 μM kainic acid (kainate binding). The membranes are then isolated by filtration. After drying of the filters, the radioactivity is measured by scintillation.

2/ Currents induced by EAA in Xenopus oocytes

Xenopus oocytes are injected with 50 ng of poly(A)$^+$ mRNA isolated from rat cerebral cortex, and incubated for 2 to 3 days at 18° C. to permit protein expression therein. The inward currents induced by EAA are measured in a medium of composition: NaCl (82.5 mM), KCl (2.5 mM), $CaCl_2$ (1 mM), $MgCl_2$ (1 mM), $NaH_2PO_4$ (1 mM), HEPES (5 mM), pH 7.4, by the 2-electrode voltage-clamp method (potential=–60 mV). For measurement of the currents induced by NMDA and glycine, $MgCl_2$ is absent from the medium and $CaCl_2$ is brought to a concentration of 2 mM. The EAA agonists that induce the currents are used at the following concentrations: kainate: 100 μm; AMPA: 30 μM; glycine/NMDA: 3/30 μM. The test product is applied 30 seconds before and during the application of the agonist.

The compounds of the present invention were studied in comparison with the most recent compounds described for their interaction with the AMPA receptor: they are 2,3-quinoxalinedione derivatives, and more especially 6-cyano-7-nitro-2,3-quinoxalinedione (CNQX) and 6-nitro-7-sulfamoylbenzo[f]quinoxaline-2,3-dione (NBQX).

The binding studies showed that the derivatives of the invention bind to the AMPA receptor with a very advantageous intensity, since the Ki is less than $10^{-6}$M.

| CNQX | Ki = 0.07 μM |
| Example 2 | Ki = 0.9 μM |

They are likewise capable of inhibiting the functional activation of the current induced by kainate and AMPA in Xenopus oocytes expressing the glutamate receptors.

| Kainate current | Example 2 | $IC_{50}$ = 2 μM |

This inhibition is strong and constant since the same $IC_{50}$ (2 μM) is found with respect to neurotoxic excitatory currents induced in the hippocampus by stimulation of the glutamatergic pathways (Schaeffer's collaterals).

Although the activity of the compounds of the invention with respect to AMPA/kainate receptors is lower than those of the quinoxalinediones, their therapeutic importance lies in the fact that they exert a selective inhibition of the AMPA receptor without affecting the NMDA receptor, which frees them from all the side effects described for the NMDA antagonists (psychotomimetic, amnesic and neurotoxic effects).

Furthermore, the compounds of the invention have an in vivo activity which is unique and exceptional for the products of this class. In fact, in the audiogenic convulsions test in DBA/$_2$ mice carried out according to the methodology described by CROUCHER et al. (Science, 216, 899, 1982), the product of Example 2 counteracts these glutamate-dependent convulsions and this protective effect is not only observed after IP administration (ID$_{50}$=18.7 mg/kg) but also after oral administration and the bioavailability index (ID$_{50}$ IP/ID$_{50}$ PO) is in the region of 0.3 whereas the quinoxalinediones such as CNQX or NBQX do not have any activity by the oral route.

The subject of the present invention is also pharmaceutical compositions containing as active principle at least one compound of formula (I), alone or in combination with one or more inert, non-toxic excipients or vehicles.

Among the pharmaceutical compositions of the invention, there may be mentioned, more especially, those which are suitable for oral, parenteral or nasal administration, simple or sugar-coated tablets, sublingual tablets, hard gelatin capsules, troches, suppositories, creams, ointments, skin gels, and the like.

The appropriate dosage varies according to the patient's age and weight, the nature and severity of the pathology and also the administration route. The latter can be oral, nasal, rectal or parenteral. Generally speaking, the single doses range between 1 and 1000 mg for a treatment administered in 1 to 3 doses per 24 hours.

The examples which follow illustrate the invention and in no way limit it. The starting materials used are known products or products prepared according to known procedures.

EXAMPLE 1

5,7-Dichloro-2(1H)-quinolone-3-phosphonic acid

Stage A: 3-Bromo-5,7-dichloro-2(1H)-quinolone 50.8 mmol of bromine are added dropwise to a suspension containing 25.4 mmol of 5,7-dichloro-2(1H)-quinolone-3-carboxylic acid in 65 ml of pyridine at 0 C. After stirring for 10 minutes at room temperature, the whole mixture is brought to 90 C. for one hour. After cooling, 300 ml of 1N hydrochloric acid are added. The expected product is obtained by filtering the precipitate, then washing the latter with 1N hydrochloric acid and with water and drying.

Melting point: >300° C.

Stage B: 3-Bromo-2,5,7-trichloroquinoline 9.2 mmol of the compound described in the preceding stage are stirred for 12 hours at reflux in 30 ml of phosphorus oxychloride. After evaporating the excess phosphorus oxychloride, the mixture is cooled in an ice bath and then hydrolysed by addition of ice-cold water. The precipitate formed is filtered, rinsed with water and dried and yields the expected product.

Melting point: 176°–181° C.

Stage C: 3-Bromo-5,7-dichloro-2-methoxyquinoline

A suspension containing 9 mmol of the compound described in the preceding stage and 20 ml of a 5.2M methanolic solution of sodium methoxide is brought to reflux for 12 hours. After cooling, the expected product is obtained after filtering the precipitate.

Melting point: 135°–138° C.

Stage D: Diethyl ester of 5,7-dichloro-2-methoxyquinol-3-ylphosphonic acid 13 mmol of triethylamine, 13 mmol of diethyl phosphite and 0.65 mmol of tetrakis(triphenylphosphine)palladium are added to 6.5 mmol of the compound described in the preceding stage in suspension in 3 ml of anhydrous tetrahydrofuran. The whole mixture is brought to reflux, under a nitrogen atmosphere, for 12 hours. The solution is then diluted in 200 ml of ethyl acetate. The organic phase is washed with 1N hydrochloric acid and then with a saturated sodium chloride solution. After drying and evaporation, the expected product is obtained after purifying the residue by chromatography on a silica column, using as eluent a cyclohexane/ethyl acetate (1/1) mixture and then ethyl acetate.

Melting point: 66°–68° C.

| | Elemental microanalysis: | | | |
|---|---|---|---|---|
| | C % | H % | N % | Cl % |
| Calculated | 46.18 | 4.43 | 3.85 | 19.47 |
| Found | 46.29 | 4.33 | 3.95 | 19.15 |

Stage E: 5,7-Dichloro-2(1H)-quinolone-3-phosphonic acid 2 ml of trimethylsilyl bromide are added to a solution containing 2 mmol of the compound described in the preceding stage in 10 ml of anhydrous acetonitrile and the whole mixture is stirred for 5 hours at reflux. After evaporation, the residue is taken up in 10 ml of 3N hydrochloric acid, the suspension is stirred for 30 minutes at 80 C. and the precipitate is filtered. The expected product is obtained after recrystallizing the precipitate from ethanol.

Melting point: >300° C.

| | Elemental microanalysis: | | | |
|---|---|---|---|---|
| | C % | H % | N % | Cl % |
| Calculated | 36.76 | 2.06 | 4.76 | 24.12 |
| Found | 36.58 | 2.16 | 4.77 | 24.18 |

EXAMPLE 2

6,7-Dichloro-2(1H)-quinolone-3-phosphonic acid

The expected product is obtained according to the process described in Example 1 by using the corresponding starting material.

Melting point: >300° C.

| | Elemental microanalysis: | | | |
|---|---|---|---|---|
| | C % | H % | N % | Cl % |
| Calculated | 36.76 | 2.06 | 4.76 | 24.12 |
| Found | 36.82 | 2.44 | 4.82 | 24.65 |

EXAMPLE 3

Monoethyl ester of 5,7-dichloro-2(1H)-quinolone-3-phosphonic acid

Stage A: Monoethyl ester of 5,7-dichloro-2-methoxyquinol-3-ylphosphonic acid.

1.3 mmol of the compound described in Stage D of Example 1 are vigorously stirred at 100 C. in 5 ml of 5N sodium hydroxide solution for 90 minutes. After cooling, the mixture is acidified with 1N hydrochloric acid. After extraction with ethyl acetate, washing the organic phase with a saturated sodium chloride solution, drying and evaporation, a colorless oil is obtained which slowly crystallizes and yields the expected product.

Melting point: 157°–158° C.

| | Elemental microanalysis: | | | |
|---|---|---|---|---|
| | C % | H % | N % | Cl % |
| Calculated | 42.88 | 3.60 | 4.17 | 21.10 |
| Found | 42.95 | 3.89 | 4.23 | 21.13 |

Stage B: Monoethyl ester of 5,7-dichloro-2(1H)-quinolone-3-phosphonic acid

A suspension containing 2.2 mmol of the compound described in the preceding stage in 16 ml of 3N hydrochloric acid is stirred for 24 hours at reflux. The precipitate formed is then filtered and yields the expected product by recrystallization from isopropanol.

Melting point: 220°–240° C.

| | Elemental microanalysis: | | | |
|---|---|---|---|---|
| | C % | H % | N % | Cl % |
| Calculated | 41.02 | 3.13 | 4.35 | 22.01 |
| Found | 41.34 | 3.16 | 4.47 | 22.14 |

EXAMPLE 4

Monoethyl ester of 6,7-dichloro-2(1H)-quinolone-3-phosphonic acid

The expected product is obtained according to the process described in Example 3 by using the corresponding starting material.

Melting point: 268°–276° C.

| | Elemental microanalysis: | | | |
|---|---|---|---|---|
| | C % | H % | N % | Cl % |
| Calculated | 41.02 | 3.13 | 4.35 | 22.01 |
| Found | 41.28 | 3.30 | 4.45 | 21.84 |

EXAMPLE 5

5,7-Dichloro-2(1H)-quinolone-3-methylphosphinic acid

Stage A: Ethyl ester of 5,7-dichloro-2-methoxyquinol-3-ylmethylphosphinic acid

A solution containing 1.49 mmol of the compound described in Stage A of Example 3 and 10 l of dimethylformamide in 15 ml of dichloromethane is stirred at 40 C. 3 mmol of oxalyl chloride diluted in 1 ml of dichloromethane are added dropwise to this solution. The whole mixture is maintained at 40 C. for one hour and then evaporated under vacuum. The residue is then dissolved in 10 ml of anhydrous tetrahydrofuran and 5801 of a 3M solution of methylmagnesium chloride in tetrahydrofuran are then added dropwise.

The reaction mixture is stirred for 90 minutes at room temperature and then hydrolysed using 1 ml of 1N hydrochloric acid. The whole mixture is diluted in 100 ml of ethyl acetate. The organic phase is washed with 1N hydrochloric acid and then with 1N sodium hydroxide solution, dried and evaporated. The expected product is obtained after purifying the residue by chromatography on a silica column, using as eluent a dichloromethane/ethanol (97/3) mixture.

Stage B: 5,7-Dichloro-2(1H)-quinolone-3-methylphosphinic acid

The expected product is obtained from the compound described in the preceding stage according to the process described in Stage E of Example 1.

Melting point: >300° C.

| | Elemental microanalysis: | | | |
|---|---|---|---|---|
| | C % | H % | N % | Cl % |
| Calculated | 41.13 | 2.76 | 4.80 | 24.28 |
| Found | 40.82 | 2.97 | 5.01 | 24.10 |

EXAMPLE 6

Monoisopropyl ester of 6,7-dichloro-2(1H)-quinolone-3-phosphonic acid

The expected product is obtained according to the process described in Example 3 by using the corresponding starting materials.

Melting point: 235°–238° C.

| | Elemental microanalysis: | | | |
|---|---|---|---|---|
| | C % | H % | N % | Cl % |
| Calculated | 42.88 | 3.60 | 4.17 | 21.10 |
| Found | 42.19 | 3.52 | 4.23 | 21.22 |

EXAMPLE 7

Monocyclopentylmethyl ester of 6,7-dichloro-2(1H)-quinolone-3-phosphonic acid

Stages A and B:

The processes described in these stages are identical to those described in Stages A and B of Example 1 from the corresponding starting material.

Stage C: 3-Bromo-6,7-dichloro-2-ethoxyquinoline

The expected product is obtained according to the process described in Stage C of Example 1 but replacing the methanolic solution of sodium methoxide with an ethanolic solution of sodium ethoxide.

Melting point: 56°–58° C.

Stage D: Monomethyl ester of 6,7-dichloro-2-ethoxyquinol-3-ylphosphonic acid 14.3 mmol of triethylamine, 14.3 mmol of dimethyl phosphite and 0.71 mmol of tetrakis(triphenylphosphine) palladium are added to a suspension containing 7.1 mmol of the compound described in the preceding stage in 5 ml of anhydrous tetrahydrofuran. The whole mixture is stirred at reflux, under nitrogen, for 12 hours. The mixture is then diluted in 200 ml of ethyl acetate. The organic phase is washed with 1N hydrochloric acid, then with a saturated sodium chloride solution and finally dried and concentrated to 20 ml. The expected product slowly crystallizes.

Melting point: 164°–166° C.

| | Elemental microanalysis: | | | |
|---|---|---|---|---|
| | C % | H % | N % | Cl % |
| Calculated | 42.88 | 3.60 | 4.17 | 21.10 |
| Found | 43.37 | 4.04 | 3.96 | 21.31 |

Stage E: Monocyclopentylmethyl ester of 6,7-dichloro-2(1H)-quinolone-3-phosphonic acid 0.42 mmol of cyclopentanemethanol and 0.42 mmol of triphenylphosphine are added to a solution containing 0.28 mmol of the compound described in the preceding stage in 2 ml of anhydrous tetrahydrofuran. After stirring for 10 minutes, 0.42 mmol of diisopropyl azodicarboxylate are added and the whole mixture is stirred for one hour at room temperature. 0.7 mmol of trimethylsilyl bromide are then added dropwise and the mixture is stirred for a further one hour at room temperature. After evaporation, the residue is taken up in 4 ml of 3N hydrochloric acid and then stirred for 12 hours at 100° C. After cooling, 20 ml of ethyl acetate are added and the two-phase mixture is stirred for 10 minutes. The white suspension which is formed is filtered and yields the expected product.

Melting point: 286°–288° C.

| | Elemental microanalysis: | | | |
|---|---|---|---|---|
| | C % | H % | N % | Cl % |
| Calculated | 47.89 | 4.29 | 3.72 | 18.85 |
| Found | 47.78 | 4.38 | 3.99 | 18.73 |

EXAMPLE 8

6-Chloro-7,8,9,10-tetrahydro-2(1H)-benzo[h]quinolone-3-phosphonic acid

The expected product is obtained according to the process described in Example 1.

Melting point: >300° C.

| | Elemental microanalysis: | | | |
|---|---|---|---|---|
| | C % | H % | N % | Cl % |
| Calculated | 49.78 | 4.18 | 4.47 | 11.30 |
| Found | 49.78 | 4.31 | 4.48 | 11.46 |

EXAMPLE 9

6-Nitro-7,8,9,10-tetrahydro-2(1H)-benzo[h]quinolone-3-phosphonic acid

The expected product is obtained according to the process described in Example 1.

Melting point: >300° C.

| | Elemental microanalysis: | | |
|---|---|---|---|
| | C % | H % | N % |
| Calculated | 48.16 | 4.04 | 8.64 |
| Found | 48.06 | 4.14 | 8.48 |

EXAMPLE 10

Monoethyl ester of 6-nitro-7,8,9,10-tetrahydro-2(1H)-benzo[h]quinolone-3-phosphonic acid The expected product is obtained according to the process described in Example 3 from the compound obtained in Stage D of Example 9.

Melting point: 268°–273° C.

| | Elemental microanalysis: | | |
|---|---|---|---|
| | C % | H % | N % |
| Calculated | 51.14 | 4.86 | 7.95 |
| Found | 50.92 | 4.71 | 7.60 |

EXAMPLE 11

10-Bromo-2(1H)-benzo[g]quinolone-3-phosphonic acid

The expected product is obtained according to the process described in Example 1.

Melting point: >300° C.

| | Elemental microanalysis: | | | |
|---|---|---|---|---|
| | C % | H % | N % | Cl % |
| Calculated | 44.10 | 2.56 | 3.96 | 22.57 |
| Found | 44.36 | 2.39 | 4.13 | 21.09 |

EXAMPLE 12

7-Nitro-2(1H)-quinolone-3-phosphonic acid

The expected product is obtained according to the process described in Example 1 by using the corresponding starting material.

Melting point: >300° C.

| | Elemental microanalysis: | | |
|---|---|---|---|
| | C % | H % | N % |
| Calculated | 40.02 | 2.61 | 10.37 |
| Found | 40.51 | 2.47 | 10.07 |

EXAMPLE 13

Di(pivaloyoxymethyl) ester of 6,7-dichloro-2(1H)-quinolone-3-phosphonic acid 7.5 mmol of triethylamine are added to a suspension containing 2.5 mmol of the compound described in Example 2 and the whole mixture is stirred for approximately 10 minutes at room temperature until complete dissolution has taken place. 7.5 mmol of chloromethyl pivalate are added dropwise to this solution and the reaction mixture is maintained overnight at 70° C. After returning to room temperature, 100 ml of ethyl acetate are added. The precipitate is filtered and rinsed with ethyl acetate and the filtrate is washed with 1N hydrochloric acid, then a saturated sodium chloride solution and dried. After evaporating the solvents under vacuum, the residual colorless oil is taken up in 15 ml of ethyl ether. The expected product then slowly crystallizes.

Melting point: 175° C.

| Elemental microanalysis: | | | | |
| --- | --- | --- | --- | --- |
| | C % | H % | N % | Cl % |
| Calculated | 48.29 | 5.02 | 2.68 | 13.58 |
| Found | 48.10 | 4.92 | 2.75 | 13.90 |

EXAMPLE 14

6,7-Difluoro-2(1H)-quinolone-3-phosphonic acid

Stage A: 3-Bromo-6,7-difluoro-2(1H)-quinolone

The expected product is obtained according to the process described in Stage A of Example 1 by replacing 5,7-dichloro-2(1H)-quinolone-3-carboxylic acid with 6,7-difluoro-2(1H)-quinolone-3-carboxylic acid.

Melting point: 265°–271° C.

Stage B: Diethyl ester of 6,7-difluoro-2(1H)-quinolone-3-phosphonic acid 42.2 mmol of triethylamine, 42.2 mmol of diethyl phosphite and 0.25 mmol of tetrakis(triphenylphosphine)-palladium are added to 21.1 mmol of the compound obtained in the preceding stage in suspension in 100 ml of anhydrous tetrahydrofuran. The reaction is stirred, at reflux under a stream of nitrogen, until the solvent has completely evaporated. The residue is then taken up in ethyl acetate. The solid formed is filtered, suspended in water and the whole mixture is stirred for 10 minutes. The expected product is obtained by filtration and drying.

Melting point: 245°–252° C.

| Elemental microanalysis: | | | |
| --- | --- | --- | --- |
| | C % | H % | N % |
| Calculated | 49.22 | 4.45 | 4.42 |
| Found | 49.07 | 4.10 | 4.56 |

Stage C: 6,7-Difluoro-2(1H)-quinolone-3-phosphonic acid

The expected product is obtained according to the process described in Stage E of Example 1 from the compound obtained in the preceding stage.

Melting point: 290°–297° C.

| Elemental microanalysis: | | | |
| --- | --- | --- | --- |
| | C % | H % | N % |
| Calculated | 41.40 | 2.32 | 5.36 |
| Found | 40.77 | 2.27 | 5.26 |

EXAMPLE 15

6,7-Diethyl-2(1H)-quinolone-3-phosphonic acid

Stage A: 3,8-Dibromo-6,7-dimethyl-2(1H)-quinolone 55.2 mmol of bromine are added dropwise to a suspension containing 9.2 mmol of 6,7-dimethyl-2(1H)-quinolone-3-carboxylic acid in 15 ml of pyridine brought to 70° C. After cooling, the whole mixture is poured into 1N hydrochloric acid. The aqueous phase is extracted with ethyl acetate. The organic phase is dried, evaporated and yields the expected product which is purified by chromatography on a silica column, using as eluent a cyclo-hexane/ethyl acetate (1/1) mixture, then ethyl acetate and finally an ethyl acetate/methanol (98/2) mixture.

Melting point: 216°–223° C.

| Elemental microanalysis: | | | | |
| --- | --- | --- | --- | --- |
| | C % | H % | N % | Br % |
| Calculated | 39.92 | 2.74 | 4.23 | 48.28 |
| Found | 40.35 | 2.72 | 4.24 | 48.21 |

Stage B: Diethyl ester of 8-bromo-6,7-dimethyl-2(1H)-quinolone-3-phosphonic acid The expected product is obtained according to the process described in Stage B of EXample 14 from the compound described in the preceding stage.

Melting point: 187°–195° C.

| Elemental microanalysis: | | | | |
| --- | --- | --- | --- | --- |
| | C % | H % | N % | Br % |
| Calculated | 46.41 | 4.93 | 3.61 | 20.58 |
| Found | 46.54 | 4.87 | 3.61 | 20.84 |

Stage C: Diethyl ester of 6,7-dimethyl-2(1H)-quinolone-3-phosphonic acid 2.5 mmol of the compound obtained in the preceding stage are hydrogenated at room temperature in 80 ml of ethanol in the presence of 150 mg of palladium-on-charcoal (5%). After filtering the catalyst and evaporation, the residue is taken up in dichloromethane. The organic phase is washed with water, dried and evaporated and yields the expected product.

Melting point: 165°–170° C.

| Elemental microanalysis: | | | |
| --- | --- | --- | --- |
| | C % | H % | N % |
| Calculated | 58.25 | 6.52 | 4.53 |
| Found | 58.16 | 6.50 | 4.51 |

Stage D: 6,7-Dimethyl-2(1H)-quinolone-3-phosphonic acid

The expected product is obtained according to the process described in Stage E of Example 1 from the product described in the preceding stage.

Melting point: >300° C.

| Elemental microanalysis: | | | |
|---|---|---|---|
| | C % | H % | N % |
| Calculated | 52.18 | 4.78 | 5.53 |
| Found | 52.05 | 4.81 | 5.60 |

Pharmacological study of the derivatives of the invention

In vivo Neuroprotective effects
1) Transient global cerebral ischemia in Gerbil

Transient and complete arrest of cerebral blood flow which is observed in clinical situation during a cardiac infarct, gives rise to a delayed death of specific vulnerable neurons, especially in hippocampus, a crucial cerebral region for cognitive functions. This phenomenon can be experimentally reproduced after transient occlusion of common carotid arteries.

In Gerbil, a transient occlusion (5 minutes) of carotid arteries gives rise to a total loss of hippocampal pyramidal neurons (CA1). This death can be observed only 3 or 4 days after ischemia. Numerous studies have shown that it could be due essentially to an excessive release of glutamate during the post-ischemic reperfusion.

Neuroprotective effects of anti-ischemic drugs can be demonstrated by histological measurement of the number of survival neurons.

NBQX (30 mg/kg IP) protects 50% of neurons in case of treatment 30 minutes before then b.i.d. after ischemia until histological measurement 4 days later.

In the same conditions, compound of example 2 (30 mg/kg IP) protects completely from neuronal death and at a smaller dose (10 mg/kg IP) protects 50% of hippocampal neurons.

2) Permanent focal ischemia in mice

In Man, the occlusion of sylvian artery (middle cerebral artery) is the cause of 70–80% of stroke cases.

This ischemia can be perfectly reproduced in mice by electrocoagulation of MCA, giving rise to a well delimited cortical infarct 24 hours later. This infarct can be easily measured by histological examination.

At 30 mg/kg IP administered before then 3 hours after ischemia, NBQX and compound of example 2 decrease significantly the infarct volume (–26%).

With the same dose administered only in curative manner (5 minutes, 1 hour and 2 hours after MCA occlusion), the compound of example 2 decreases the infarct volume (–23%) and on the contrary NBQX remains ineffective.

EXAMPLE 17

Pharmaceutical composition

| Preparation formula for 1000 tablets containing a dose of 10 mg | |
|---|---|
| Compound of Example 2 | 10 g |
| Hydroxypropylcellulose | 2 g |
| Wheat starch | 10 g |
| Lactose | 100 g |
| Magnesium stearate | 3 g |
| Talc | 3 g |

We claim:
1. A method for treating cerebral ischemia in a mammal, comprising the step of administering to the mammal an amount of a compound selected from those of formula (I):

[Structure of formula (I): a quinolone with substituents $R_1$, $R_2$, $R_3$ on the benzene ring, and at the 3-position a phosphonate group $P(=O)(OR_4)(R_5)$, with N-H and C=O in the quinolone ring]

in which:
$R_1$, $R_2$, and $R_3$, which are identical or different, represent hydrogen, halogen, linear or branched ($C_1$–$C_6$) alkyl which is unsubstituted or substituted with one or a number of halogen atoms or nitro, cyano, or aminosulfonyl groups,
or alternatively, when two of $R_1$, $R_2$, and $R_3$, are located on adjacent carbons, form, with the carbon atoms to which they are attached, a ($C_3$–$C_7$) cycloalkene ring or a benzene ring which is unsubstituted or substituted with one or a number of halogen atoms or linear or branched ($C_1$–$C_6$) alkyl, linear or branched ($C_1$–$C_6$) alkoxy, or trihalomethyl groups,
$R_4$ represents hydrogen, linear or branched ($C_1$–$C_6$) alkyl, phenyl which is unsubstituted or substituted with one or a number of halogen atoms or linear or branched ($C_1$–$C_6$) alkyl, linear or branched ($C_1$–$C_6$) alkoxy, or trihalomethyl, or a group $$R_7-CO-O-\underset{R_6}{CH}-$$

in which $R_6$ and $R_7$, which are identical or different, represent a hydrogen atom or linear or branched ($C_1$–$C_6$) alkyl, which is unsubstituted or substituted with ($C_3$–$C_7$) cycloalkyl or with phenyl,
$R_5$ represents hydrogen, hydroxyl, linear or branched ($C_1$–$C_6$) alkoxy, phenoxy, mercapto, linear or branched ($C_1$–$C_6$) alkylthio, linear or branched ($C_1$–$C_6$) alkyl which is unsubstituted or substituted with ($C_3$–$C_7$) cycloalkyl, phenyl which is unsubstituted or substituted with one or a number of halogen atoms or with linear or branched ($C_1$–$C_6$) alkyl, linear or branched ($C_1$–$C_6$) alkoxy, or trihalomethyl, or amino which is unsubstituted or substituted with one or two linear or branched ($C_1$–$C_6$) alkyl, or a group $$R_7-CO-O-\underset{R_6}{CH}-C-$$

in which $R_6$ and $R_7$ are as defined above,
its isomers, and its addition salts with a pharmaceutically-acceptable acid or base, which is effective for alleviation of said condition.
2. The method of claim 1 wherein at least one of the groups $R_1$, $R_2$, and $R_3$ represents chlorine.
3. The method of claim 1 wherein $R_4$ represents hydrogen.
4. The method of claim 1 wherein $R_5$ represents hydroxyl.
5. The method of claim 1 wherein the compound is 6,7-dichloro-2(1H)-quinolone-3-phosphonic acid.

6. The method of claim 1, wherein an effective amount of the compound is administered in admixture with one or more pharmaceutically-acceptable excipients or vehicles.

7. The method of claim 1 wherein the compound is 6-chloro-7,8,9,10-tetrahydro-2(1H)-benzo[h]quinolone-3-phosphonic acid.

8. The method of claim 6 wherein the compound is 6-nitro-7,8,9,10-tetrahydro-2(1H)-benzo[h]quinolone-3-phosphonic acid.

9. The method of claim 1 wherein the compound is monoethyl ester of 6-nitro-7,8,9,10-tetrahydro-2(1H)-benzo[h]quinolone-3-phosphonic acid.

* * * * *